United States Patent [19]

Müller et al.

[11] 4,364,869

[45] Dec. 21, 1982

[54] PROCESS FOR PRODUCING ALKYL ESTERS OF SATURATED ALIPHATIC CARBOXYLIC ACIDS

[75] Inventors: Wolfgang H. E. Müller; Peter Hofmann, both of Marl, Fed. Rep. of Germany

[73] Assignee: Chemische Werke Hüls A.G., Marl, Fed. Rep. of Germany

[21] Appl. No.: 288,065

[22] Filed: Jul. 29, 1981

[30] Foreign Application Priority Data

Sep. 12, 1980 [DE] Fed. Rep. of Germany ....... 3034420

[51] Int. Cl.$^3$ .......................... B01D 3/36; C11C 3/12; C07C 67/48
[52] U.S. Cl. ............................... 260/410.9 R; 203/61; 560/114; 560/204; 560/232; 560/248
[58] Field of Search .............................. 546/353, 251; 260/410.9 R; 560/114, 204, 232, 233, 248; 203/61, 58

[56] References Cited

U.S. PATENT DOCUMENTS

| | | | |
|---|---|---|---|
| 2,412,650 | 12/1946 | Riethof | 203/61 |
| 2,412,651 | 12/1946 | Riethof | 203/61 |
| 2,511,198 | 6/1950 | Engel | 546/353 |
| 3,507,891 | 4/1970 | Hearne | 260/410.9 |
| 3,906,016 | 9/1975 | Isa | 260/410.9 R |
| 4,041,057 | 8/1977 | Fanning | 260/410.9 R |

FOREIGN PATENT DOCUMENTS 949194 2/1964 United Kingdom .

OTHER PUBLICATIONS

Peter Hofmann et al., "Hydrocarboxymethylation—An Attractive Route from Olefins to Fatty Acid Esters?" Sep. 1980, I and EC Product Research and Development, vol. 19, pp. 330–334.

*Primary Examiner*—Wilbur L. Bascomb, Jr.
*Attorney, Agent, or Firm*—Wells & Wells

[57] ABSTRACT

A process for the production of alkyl esters of saturated aliphatic carboxylic acids by reacting in an alkoxycarbonylation stage olefins with carbon monoxide and alkanol in the presence of a catalyst consisting of a cobalt compound and a promoter from the group of pyridine, non-ortho-substituted alkylpyridine or mixtures thereof at elevated pressure and elevated temperature. The reaction mixture produced is reprocessed and the pyridine, non-ortho-substituted alkylpyridine, or mixture used as the promoter is rectified prior to its feedback into the alkoxycarbonylation stage in the presence of a given carboxylic acid which is thermally stable under the conditions of reprocessing and which forms a maximum azeotrope with the promoter under the conditions of rectification.

7 Claims, No Drawings

PROCESS FOR PRODUCING ALKYL ESTERS OF SATURATED ALIPHATIC CARBOXYLIC ACIDS

CROSS-REFERENCE TO RELATED APPLICATIONS

Applicants claim priority under 35 USC 119 for application No. P 30 34 420.8, filed Sept. 12, 1980 in the Patent Office of the Federal Republic of Germany.

The disclosure of coinventor Hofmann's copending application Ser. No. 125,482, filed Feb. 28, 1980 is incorporated herein to show alkoxycarbonylation procedures carried out in the presence of cobalt catalysts and a promoter from the group pyridine, non-ortho-substituted alkylpyridine and mixtures thereof.

Also incorporated herein is coinventor Hofmann's copending application Ser. No. 203,393, filed Nov. 3, 1980 to show that olefins with internal double bonds can be produced by dehydrogenation of paraffins or by chlorination followed by dehydrochlorination of paraffins.

BACKGROUND OF THE INVENTION

The field of the invention is the production of alkyl esters of saturated aliphatic carboxylic acids and the present invention is particularly concerned with reacting olefins with carbon monoxide and alkanol in the presence of a catalyst consisting of a cobalt compound and a promoter selected from pyridine, non-ortho-substituted alkylpyridine or mixtures thereof at elevated pressures and elevated temperatures.

The state of the art of such alkoxycarbonylation reactions may be ascertained by reference to U.S. Pat. Nos. 3,507,891; 3,906,016; and 4,041,057 and the article "Hydrocarboxymethylation—an Attractive Route from Olefins to Fatty Acid Esters?", by Peter Hofmann et al. as published in I & EC Product Research and Development, Vol. 19, September 1980, pp. 330-334, the disclosures of which are incorporated herein.

It is known that by reacting olefins with carbon monoxide and a compound having a replaceable hydrogen atom such as an alkanol in the presence of a catalyst containing a metal of Group VIII of the Periodic Table of elements and possibly a promoter, fatty acid esters can be produced as disclosed in J. Falbe, Synthesen mit Kohlenmonoxid, Springer publishers, Berling, Heidelberg, New York (1967).

A preferred variation of this reaction, which is termed alkoxycarbonylation, is the conversion in the presence of cobalt catalysts. An especially preferred implementation is found to be the additional use of pyridine, non-ortho-substituted alkylpyridine or mixtures thereof as promoter, as disclosed in U.S. Pat. No. 3,507,891.

A substantive problem in this homogeneously catalyzed reaction is the recovery of the relatively expensive pyridine, non-ortho-substituted alkylpyridine and mixtures thereof from the reaction mixture in such a form as to allow reuse as promoter.

West German Published Application No. 19 63 804 and U.S. Pat. No. 3,507,891 disclose only that the promoter separation can be carried out by distillation.

However, as shown by applicants' own experiments, there is a drop in conversion when a promoter so recovered is reused a number of times. This drop in conversion may be attributed to a deactivation of the catalytic system, mainly by an enrichment in substances acting in an inhibiting manner in the fed back or recycled promoter. However, prior art attempts to remove these inhibitors, manifestly present in low quantities, by distillation at an economically justifiable cost have failed.

SUMMARY OF THE INVENTION

Having in mind the limitations of the prior art it is an object of the present invention to create a process permitting the purification of pyridine, non-ortho-substituted alkylpyridine and mixtures thereof used as the catalytic component (promoter) in a simple and economical manner so that it can be fed back into the alkoxycarbonylation process without degrading the activity of the catalytic system.

This object is achieved according to the present invention in a process for the production of alkyl esters of saturated aliphatic carboxylic acids where olefins are reacted with carbon monoxide and alkanol in the presence of a catalyst consisting of a cobalt compound and a promoter consisting of pyridine, non-ortho-substituted alkylpyridine or mixtures thereof at elevated pressure and elevated temperature to produce a reaction mixture.

By elevated pressure is meant pressures of about 10 to 800 and preferably about 100 to 300 bars.

By elevated temperature is meant a temperature of about 80 to 300 and preferably about 150° to 220° C.

The reaction mixture is reprocessed, the pyridine, non-ortho-substituted alkylpyridine or mixtures thereof is used as the catalytic component (promoter) and is rectified prior to its feedback into the alkoxycarbonylation stage in the presence of a carboxylic acid which is thermally stable under the conditions of reprocessing and which forms a maximum azeotrope with pyridine, non-ortho-substituted alkylpyridine or mixture under the conditions of rectification.

DESCRIPTION OF THE PREFERRED EMBODIMENTS

In principle the process of the present invention applies to all alkoxycarbonylation methods for the production of fatty acid esters wherein a catalyst consisting of a cobalt compound and pyridine, a non-ortho-substituted alkylpyridine or mixture is used as disclosed in U.S. Pat. No. 3,507,891 and U.S. patent application Ser. No. 125,482. Most of all, the selection of the olefin used is noncritical, that is, both straight-chain or branched alpha-olefins and olefins with an internal double bond can be used. Moreover, olefins with more than one double bond and those with specific substituents, for instance aryl groups, are also suitable.

As a rule olefins having 2 to 40, preferably 4 to 20, especially preferred olefins with 10 to 18 C atoms are used, which may be obtained by methods of the state of the art. For instance, alpha-olefins are obtained by the Ziegler oligomerization of ethylene as disclosed in German Pat. No. 878,560 and U.S. Pat. No. 3,310,600, or by wax cracking. Olefins with an internal double bond can be produced by dehydrogenation or by chlorination with ensuing dehydrochlorination of paraffins, as discosed in U.S. patent application Ser. No. 203,393 and British Pat. No. 1,037,868.

As regards the last cited method, blends of paraffins are used as a rule, i.e., mixtures of different C numbers, whereby the olefins that are obtained in turn also lack a uniform C number.

Moreover and naturally, all conceivable isomeric forms are present in these olefin mixtures. Besides the use of pure and possibly substituted olefins, it is also possible to use olefin mixtures with a paraffin content for instance up to 85% by weight. This paraffin content results because complete conversion is not achieved in the production of olefins, and the unconverted paraffins are not separated, or are only incompletely separated.

Besides the olefin being used being noncritical for the process of the present invention, so is also the kind of alkanol which is being reacted with the olefin and carbon monoxide. As a rule, alkanols having 1 to 20, preferably 1 to 3 C atoms are used. Typically representative substances from the group of the primary alkanols are, for instance, methanol, ethanol and propanol-(1).

It is again immaterial which cobalt compound is used in the alkoxycarbonylation. Cobalt carbonyls such as dicobaltoctacarbonyl are just as suitable as carboxylic-acid cobalt salts such as cobalt acetate, cobalt naphthenate and cobalt-2-ethylhexanoate, and salts of cobalt with inorganic acids such as cobalt nitrate and cobalt sulfate. Preferably those carboxylic acid cobalt salts are used, where the anions correspond to the acid residue of the fatty acids formed in the alkoxycarbonylation.

In addition to pyridine alone or in a mixture, applicable promoters are all non-ortho-substituted alkylpyridines such as 3-picoline, 4-picoline, 3,4-dimethylpyridine and 3,5-dimethylpyridine and 3-ethylpyridine and 4-ethylpyridine.

Again, the conditions of reaction in which the alkoxycarbonylation is carried out are not significant for the process of the present invention. In general, the alkoxycarbonylation processes are carried out at temperatures of about 80 to 300, preferably 150° to 220° C., and at carbon monoxide pressures of about 10 to 800, preferably 100 to 300 bars.

Lastly, it is not critical with respect to the present process, though advantageous, that the reaction mixture prior to its further processing be treated with oxygen or a gas containing oxygen, preferably air, at temperatures of about 20 to 150, preferably 50° to 120° C. This treatment, which already has been described in U.S. Pat. No. 3,507,891, Column 4, lines 21–43 and in U.S. patent application Ser. No. 203,393, which is not yet part of the state of the art, page 5, last paragraph, is carried out until cobalt compounds resulting in the subsequent processing by distillation in the separation of metallic cobalt have been destroyed by oxidation.

In the ensuing processing by distillation, the unconverted alkanol and olefin, the promoter and the reaction products are separated in one step or stepwise at sump temperatures up to 350° C. The stepwise processing is preferred because in this manner fractions are obtained which, except for the fatty acid esters, can be fed back into the process at suitable locations.

Now it has been surprisingly found that by means of the steps of the present invention, the pyridine, non-ortho-substituted alkylpyridine and mixtures used as the catalytic component can be purified by rectification to such an extent that even for an often repeated feedback of the promoter into the alkoxycarbonylation stage, that is, into the actual ester synthesis, no detectable drop in activity of the catalytic systems was found.

What is important is that the carboxylic acid used in the process of the present invention shall meet definite requirements. First, it must be thermally stable under the conditions of processing the reaction mixture. Moreover, the carboxylic acid must form a maximum azeotrope (boiling point maximum) with the promoter for the conditions of reaction applying to the promoter recovery.

When the process of the present invention is applied to those alkoxycarbonylation methods in which the olefins contain 10 to 18 C atoms, the alkanols 1 to 3 C atoms and the promoters are pyridine, 3-picoline, 4-picoline, 3,4-dimethylpyridine, 3,5-dimethylpyridine, 3-ethylpyridine or 4-ethylpyridine or mixtures thereof, it is advantgeous that the carboxylic acid, or the azeotrope of this carboxylic acid with the hydrocarbons present (olefins and possibly paraffins) be of a boiling point lower than that of the hydrocarbons. In this manner it is possible to separate the promoter from the hydrocarbons and to purify the promoter by means of the carboxylic acid in a rectification stage.

In principle, all those carboxylic acids are useful in the process of the present invention which meet the stated conditions. Especially well suited are acetic acid, propionic acid and n-butyric acid and iso-butyric acid.

To avert contaminating the fed back promoter with carboxylic acid, the carboxylic acid should at the latest be added during rectification of the promoter in such an amount which will be less than that corresponding to the azeotropic composition in the system of carboxylic-acid/pyridine, non-ortho-substituted alkylpyridine or mixtures under the conditions of rectification and amounting at least to 5 ppm (weight) referred to the hourly rate of pyridine, non-ortho-substituted alkypyridine or mixture.

As a rule, the process of the present invention, which can be carried out both discontinuously and continuously, is implemented as follows:

The reaction mixture leaving the alkoxycarbonylation stage is first treated with oxygen or a gas containing oxygen, preferably air, to destroy the volatile cobalt compound. Thereupon, the reaction mixture is separated to the extent required and preferably by distillation in accordance with its composition and the location of the boiling points of the individual components. The unconverted input materials (olefin, alkanol, promoter and cobalt compound) where appropriate and following removal of partial amounts and purification or reprocessing, are fed back into the alkoxycarbonylation stage. As regards the separation and the purification of the promoter, these steps can be carried out in single and multi-stages, for instance, two stages, depending on the composition of the reaction mixture. Depending on the separation and purification of the promoter being carried out in one or more stages, the substances acting as inhibitors and to be removed will collect together with the carboxylic acid previously supplied in continuous or discontinuous manner either at the central part or in the sump of the rectification column. They may be removed both in liquid and gaseous form, discontinuously or continuously, and then be discarded. Further particulars relating to the implementation of the process of the present invention may be found for instance in the monograph "Industrielle Destillation" by Reinhard Billet, Chemie publishers, Weinheim (1973).

The process of the present invention is discussed below in closer detail in relation to the following examples.

EXAMPLE 1

After the reactor discharge obtained from the reaction of a predominantly linear $C_{11}$–$C_{13}$ olefin blend with methanol and carbon monoxide comprising cobalt and picoline-4 as the catalytic components using the socalled alkoxycarbonylation method and following the destruction of the volatile cobalt compounds by oxidation, the reaction mixture was separated into a cobalt-free distillate containing the predominant amount of the volatile substances of the raw product and a concentrate containing all of the cobalt that was present in the raw product. The methanol still remaining in the raw product and also slight amounts of substances with boiling points lower than that of picoline-4 first were separated from the cobalt-free distillate by continuous rectification.

The remaining product, which consists mainly of picoline-4, $C_{11}$–$C_{13}$ olefins, $C_{11}$–$C_{13}$ paraffins and of the desired $C_{12}$–$C_{14}$ carboxylic acid methyl esters, was rectified continuously in a column with 65 practical plates and a pressure at the column top of 40 mbars. The inflow was fed in liquid form at the boiling point temperature to the 45th plate from below. The picoline-4 was removed at the top of the column at a return ratio of 5. The hydrocarbons, the carboxylic acid methyl esters and slight amounts of higher boiling points of unknown structure and separated in further rectifications, were removed from the sump of the column. The temperature at the top of the column was 56° C., that at the sump was 148° C., and the pressure difference across the column was 85 mbars. The temperature profile of the rectification column is state in Column 1 of Table 1.

Together with the input, 0.05% by weight of acetic acid referred to the picoline present, were continuously fed into the column. Referred to the total amount of picoline supplied, 0.15% by weight of a mixture which following condensation forms two liquid phases were removed in vapor form from the 40th tray, as computed from below, in order to avert an enrichment of the degrading substances and of the acetic acid in the column. Under these conditions, the activity and the selectivity of the catalytic systems remained unaltered for 50 complete feedback actions of the picoline and the cobalt into the synthesis.

CONTROL EXAMPLE (COMPARISON TEST)

Following a procedure precisely corresponding to that of Example 1, but wherein no acetic acid is fed into the continuously operating rectification column, and no product at all is removed from the 40th tray of the column, a stationary temperature profile as listed in the 2nd column of Table 1 set in. After the recovered picoline had been fed back 20 times into the synthesis, a drop in activity of the catalytic system to 62% of the initial activity was determined, and after 30 feedbacks, a drop down to 39% of the initial activity.

EXAMPLE 2

Following the procedure corresponding to Example 1, however, without any acetic acid in the input of the continuously operating rectification column, rather 0.05% by weight of butyric acid were introduced, referred to the amount of picoline supplied to the column on the 50th plate counted from below, and wherein as in Example 1 there were removed 0.15% by weight of a vapor product from the 40th plate, a temperature profile as listed in the third column of Table 1 set in. The activity and the selectivity of the catalytic system remained unaltered in the alkoxycarbonylation reaction even after 32 complete feedbacks of the cobalt and the picoline.

TABLE 1

| Example No. | 1 | 2 | 3 |
|---|---|---|---|
| Total Number of plates | 65 | 65 | 65 |
| Supply plates (counted from below) | 45 | 45 | 45 |
| Discharge plates (counted from below) | 40 | 40 | 40 |
| Butyric acid supply (plates counted from below) | — | — | 50 |
| Pressure in Column head (mbars) | 40 | 40 | 40 |
| Pressure in column sump (mbars) | 125 | 125 | 125 |
| Return ratio | 5 | 5 | 5 |
| Temperature at column top | 56 | 56 | 56 |
| Temperature of 60th plate | 59 | 59 | 59 |
| Temperature of 55th plate | 70 | 62 | 92 |
| Temperature of 50th plate | 79 | 65 | 103 |
| Temperature of 45th plate | 86 | 80 | 111 |
| Temperature of 43rd plate | 92 | 83 | 112 |
| Temperature of 40th plate | 94 | 89 | 113 |
| Temperature of 30th plate | 105 | 108 | 115 |
| Temperature of 20th plate | 117 | 117 | 117 |
| Temperature of 10th plate | 125 | 126 | 126 |
| Sump Temperature | 148 | 148 | 148 |

We claim:

1. A process for the production of alkyl esters of saturated aliphatic carboxylic acids, comprising:
   (a) reacting in an alkoxycarbonylation stage starting material olefins with carbon monoxide and alkanols in the presence of a catalyst consisting of a cobalt compound and a promoter selected from the group consisting of pyridine, non-otho-substituted alkylpyridine or mixtures thereof at an elevated pressure of about 10 to 800 bars and an elevated temperature of about 80° to 300° C. to produce a reaction mixture containing reaction products which include said alkyl esters, said cobalt compound, said promoter, and unreacted starting material;
   (b) separating said cobalt compound from said reaction mixture;
   (c) adding a given carboxylic acid to said reaction mixture separated from said cobalt compound, said carboxylic acid being thermally stable and forming a maximum azeotrope with said promoter under rectification;
   (d) rectifying said reaction mixture containing said carboxylic acid and free of said cobalt compound and separating by rectification said azeotrope containing said carboxylic acid and said promoter; and
   (e) feeding said separated promoter to said alkoxycarbonylation stage.

2. The process of claim 1, wherein said carboxylic acid is added in an amount which is less than that corresponding to the azeotropic composition in the system carboxylic acid/promoter under the conditions of rectification and which amounts to at least 5 ppm by weight referred to the hourly rate of promoter supplied.

3. The process of claim 2, wherein said olefins have 10 to 18 C atoms, said alkanols have 1 to 3 C atoms, said promoter is selected from the group consisting of pyridine, 3-picoline, 4-picoline, 3,4-dimethylpyridine, 3,5-dimethylpyridine, 3-ethylpyridine, 4-ethylpyridine or mixtures thereof, and said carboxyic acid forms a maximum azeotrope with said promoter and a minimum azeotrope with any hydrocarbons present or boils at a lower point than these.

4. The process of claim 2, wherein said olefins have 10 to 18 C atoms, said alkanols have 1 to 3 C atoms, said promoter is selected from the group consisting of pyridine, 3-picoline, 4-picoline, 3,4-dimethylpyridine, 3,5-dimethylpyridine, 3-ethylpyridine, 4-ethylpyridine, or mixtures thereof, and said carboxylic acid forms a maximum azeotrope with said promoter and boils at a lower point than said promoter.

5. The process of claim 1, wherein said carboxylic acid has 2 to 4 C atoms.

6. The process of claim 5, wherein said carboxylic acid is acetic acid.

7. The process of claim 1, wherein step (b) is carried out by treating with an oxygenated gas at a temperature of about 20° to 150° C.

* * * * *